(12) United States Patent
Heck et al.

(10) Patent No.: US 7,507,256 B2
(45) Date of Patent: *Mar. 24, 2009

(54) MODULAR IMPLANT SYSTEM AND METHOD WITH DIAPHYSEAL IMPLANT

(75) Inventors: Robert K. Heck, Memphis, TN (US); Stephen A. Hazebrouck, Winona Lake, IN (US)

(73) Assignee: Depuy Products, Inc., Warsaw, IN (US)

( * ) Notice: Subject to any disclaimer, the term of this patent is extended or adjusted under 35 U.S.C. 154(b) by 148 days.

This patent is subject to a terminal disclaimer.

(21) Appl. No.: 11/300,069

(22) Filed: Dec. 14, 2005

(65) Prior Publication Data

US 2006/0167554 A1    Jul. 27, 2006

Related U.S. Application Data

(60) Provisional application No. 60/732,402, filed on Oct. 31, 2005, provisional application No. 60/731,999, filed on Oct. 31, 2005, provisional application No. 60/637,015, filed on Dec. 17, 2004.

(51) Int. Cl.
*A61F 2/38* (2006.01)
(52) U.S. Cl. ............... 623/20.15; 623/22.42; 623/23.24
(58) Field of Classification Search ................ 623/23.5, 623/23.18, 22.42, 20.15, 20.16, 20.17, 20.34, 623/20.36, 22.41, 23.15, 23.21–23.36, 23.44–23.46; 606/62, 67
See application file for complete search history.

(56) References Cited

U.S. PATENT DOCUMENTS

| | | | |
|---|---|---|---|
| 3,605,123 A | 9/1971 | Hahn | |
| 3,848,272 A | 11/1974 | Noiles | |
| 4,219,893 A | 9/1980 | Noiles | |
| 4,301,553 A | 11/1981 | Noiles | |
| 4,384,373 A | 5/1983 | Sivash | |
| 4,502,160 A | 3/1985 | Moore et al. | |
| 4,676,797 A | 6/1987 | Anapliotis et al. | |
| 4,787,907 A | 11/1988 | Carignan | |
| 4,790,852 A | 12/1988 | Noiles | |
| 4,822,366 A | 4/1989 | Bolesky | |
| 4,846,839 A * | 7/1989 | Noiles | ..................... 623/23.46 |
| 4,938,768 A | 7/1990 | Wu | |

(Continued)

OTHER PUBLICATIONS

DePuy Orthopaedics, Inc., M.B.T. Revision Tray, 2004, DePuy Orthopaedics, Inc., Warsaw, Indiana.

(Continued)

*Primary Examiner*—Bruce E Snow
*Assistant Examiner*—Megan Wolf

(57) ABSTRACT

A modular implant system allows a surgeon to secure an implant assembly to thee diaphysis of a long bone. The system includes a set of anatomically-designed diaphyseal fitting modular implant components. One end of each diaphyseal implant component is a Morse taper post for connection to another implant component such as a modular articular component, a segmental component or an intercalary component. The other end of each diaphyseal component is a tapered porous surface. In some sizes, the tapered porous surface includes a plurality of steps. The tapered porous surface is received with a tapered bore in the bone diaphysis that is prepared to match the size and shape of the tapered porous surface. The diaphyseal implant is easy to insert and remove, does not bind before fully seating, is designed to prevent stress shielding and provides the surgeon with a host of stem options with its modularity.

21 Claims, 9 Drawing Sheets

U.S. PATENT DOCUMENTS

| | | | |
|---|---|---|---|
| 5,032,130 A | 7/1991 | Schelhas et al. | |
| 5,080,685 A | 1/1992 | Bolesky et al. | |
| 5,152,796 A | 10/1992 | Slamin | |
| 5,181,928 A | 1/1993 | Bolesky et al. | |
| 5,286,260 A | 2/1994 | Bolesky et al. | |
| 5,330,534 A | 7/1994 | Herrington et al. | |
| 5,358,524 A | 10/1994 | Richelsoph | |
| 5,370,706 A | 12/1994 | Bolesky et al. | |
| 5,653,765 A | 8/1997 | McTighe et al. | |
| 5,658,349 A | 8/1997 | Brooks et al. | |
| 5,782,921 A | 7/1998 | Colleran et al. | |
| 5,824,097 A | 10/1998 | Gabriel et al. | |
| 5,876,459 A | 3/1999 | Powell | |
| 5,906,644 A | 5/1999 | Powell | |
| 6,071,311 A | 6/2000 | O'Neil et al. | |
| 6,102,956 A | 8/2000 | Kranz | |
| 6,171,342 B1 | 1/2001 | O'Neil | |
| 6,214,052 B1 | 4/2001 | Burkinshaw | |
| 6,264,699 B1 | 7/2001 | Noiles et al. | |
| 6,428,578 B2 | 8/2002 | White | |
| 6,527,807 B1 | 3/2003 | O'Neil et al. | |
| 6,613,092 B1 | 9/2003 | Kana et al. | |
| 6,692,530 B2 | 2/2004 | Doubler et al. | |
| 6,712,858 B1 | 3/2004 | Grundei et al. | |
| 6,723,129 B2 | 4/2004 | Dwyer et al. | |
| 6,786,931 B2 | 9/2004 | Hazebrouck | |
| 6,824,566 B2 | 11/2004 | Kana et al. | |
| 6,866,683 B2 | 3/2005 | Gerbec et al. | |
| 6,875,239 B2 | 4/2005 | Gerbec et al. | |
| 6,902,583 B2 | 6/2005 | Gerbec et al. | |
| 7,175,664 B1 * | 2/2007 | Lakin | 623/19.14 |
| 2003/0204267 A1 | 10/2003 | Hazebrouck | |
| 2004/0193267 A1 | 9/2004 | Jones | |
| 2004/0193268 A1 | 9/2004 | Hazebrouck | |
| 2005/0107794 A1 | 5/2005 | Hazebrouck | |
| 2005/0107883 A1 | 5/2005 | Goodfried | |
| 2006/0041317 A1 | 2/2006 | Hazebrouck | |
| 2006/0167560 A1 * | 7/2006 | Heck et al. | 623/23.46 |

OTHER PUBLICATIONS

DePuy Orthopaedics, Inc., S-ROM Noiles Rotating Hinge, 2002, DePuy Orthopaedics, Inc., Warsaw, Indiana.

Biomet, Orthopaedic Salvage System Overview, date unknown, admitted prior art.

DePuy, Reconstructive/Revision Products, date unknown, admitted prior art.

* cited by examiner

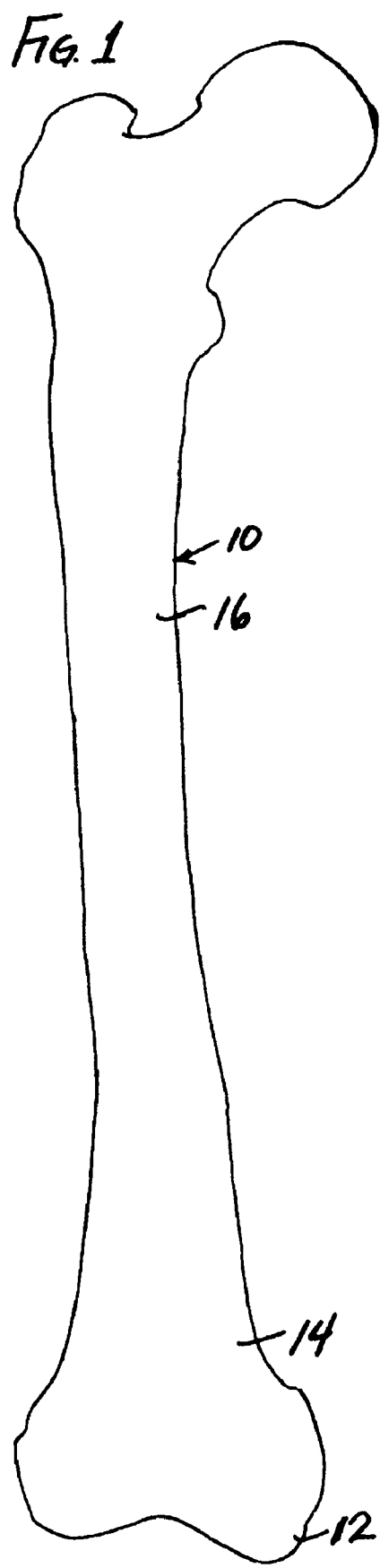
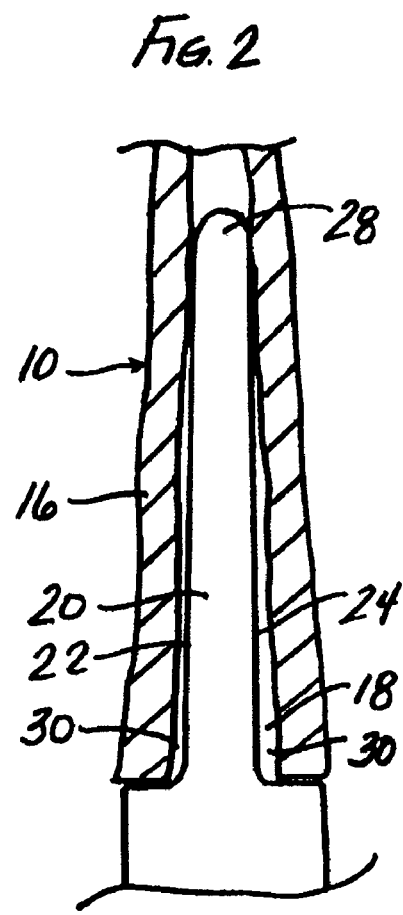

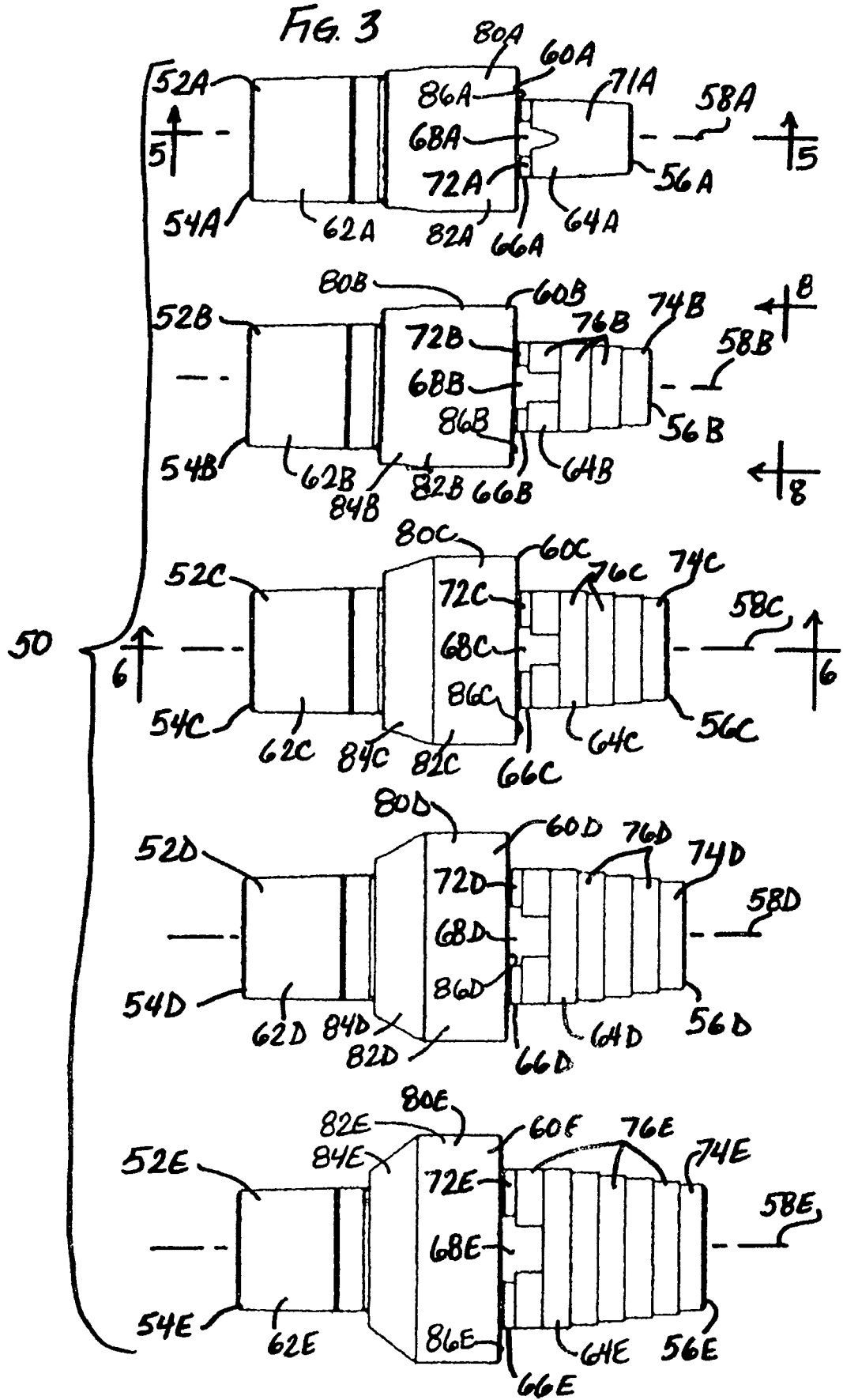

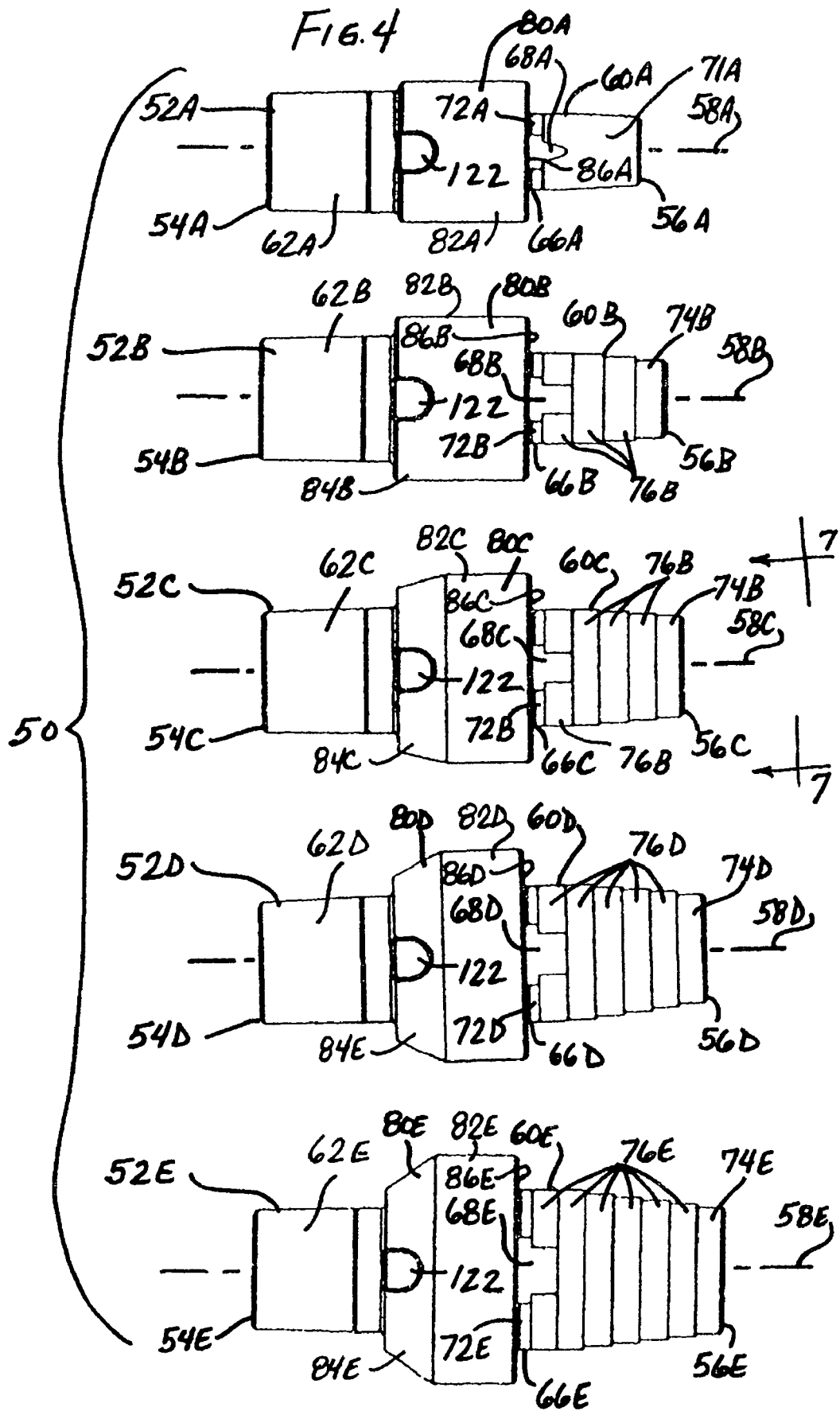

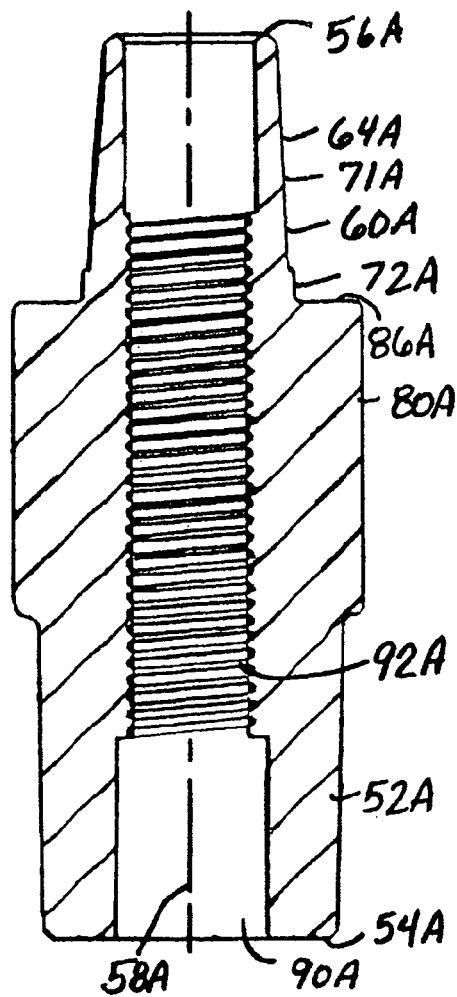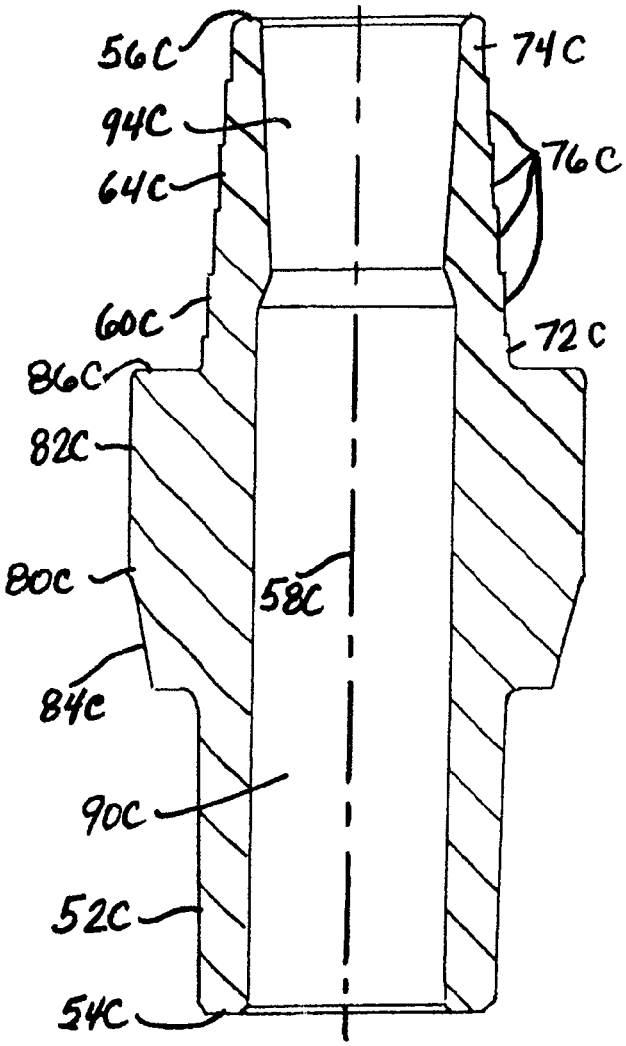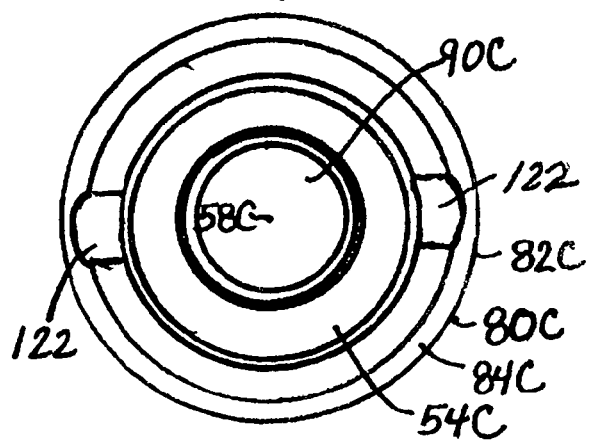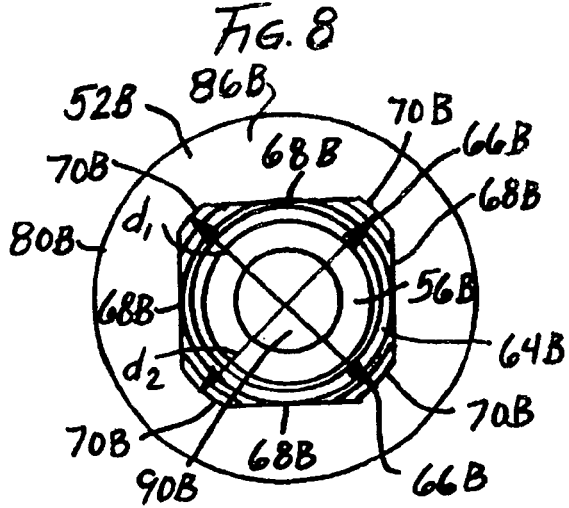

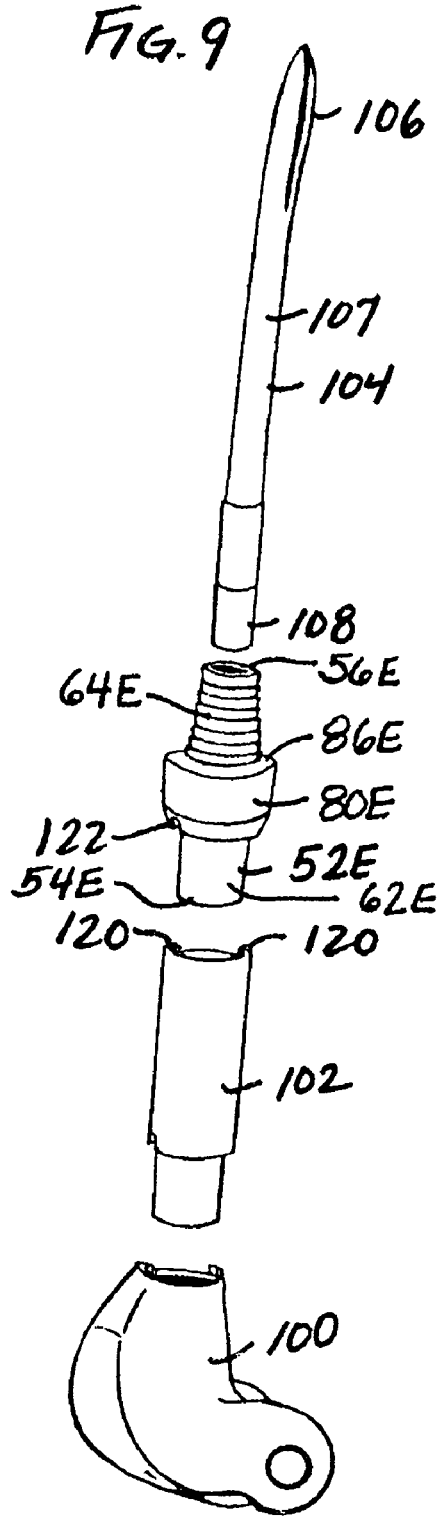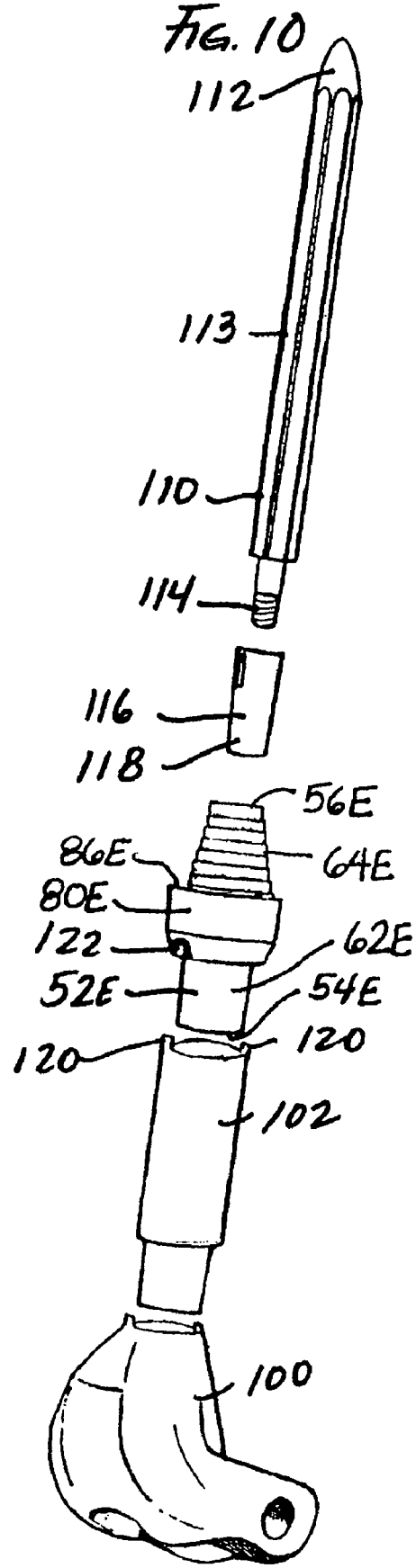

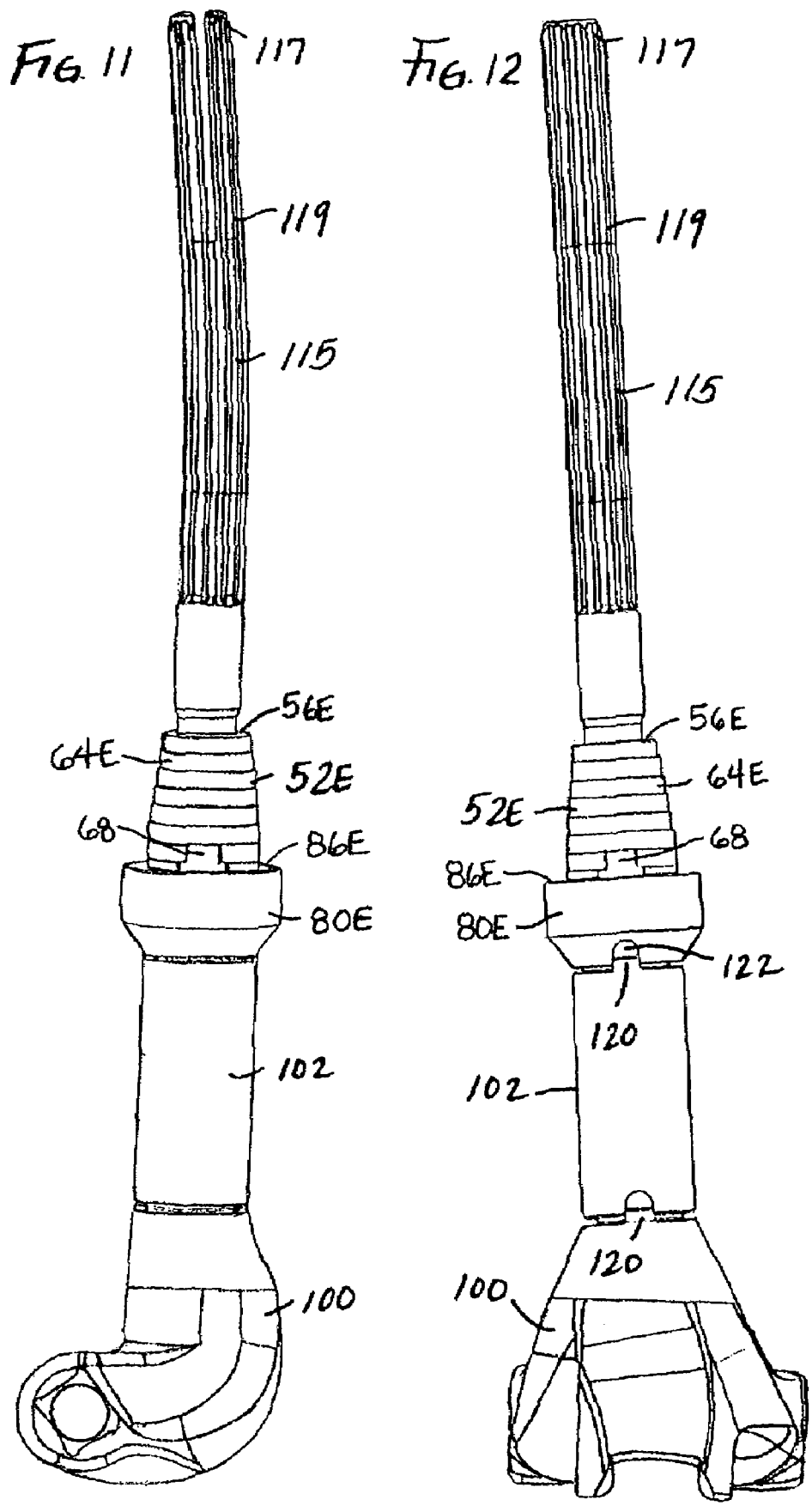

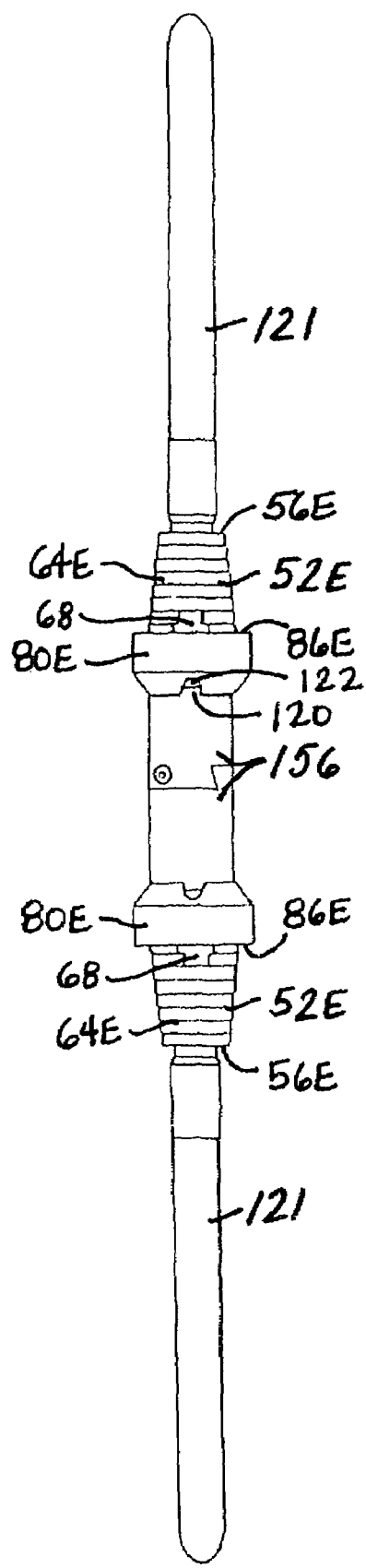
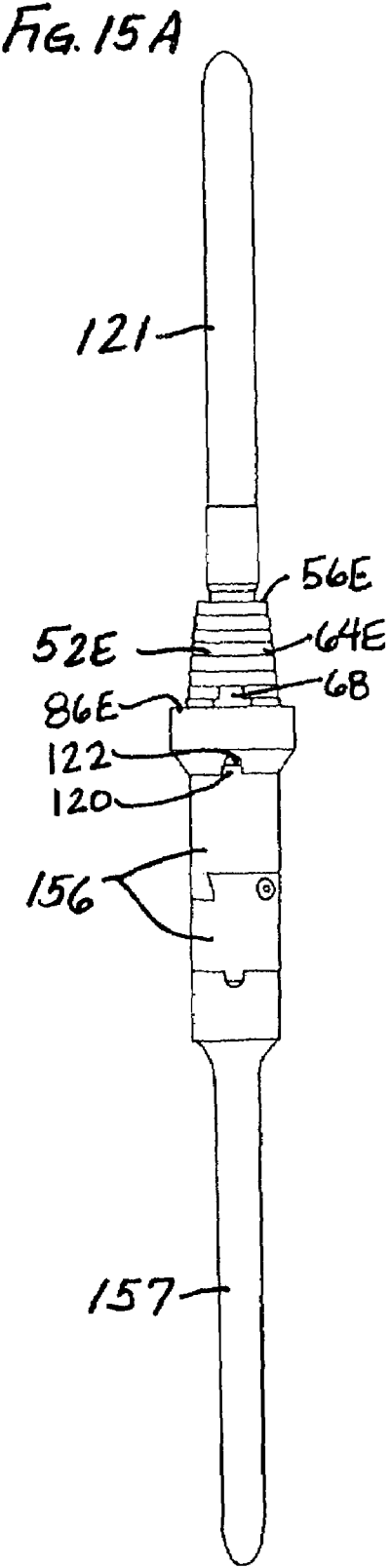

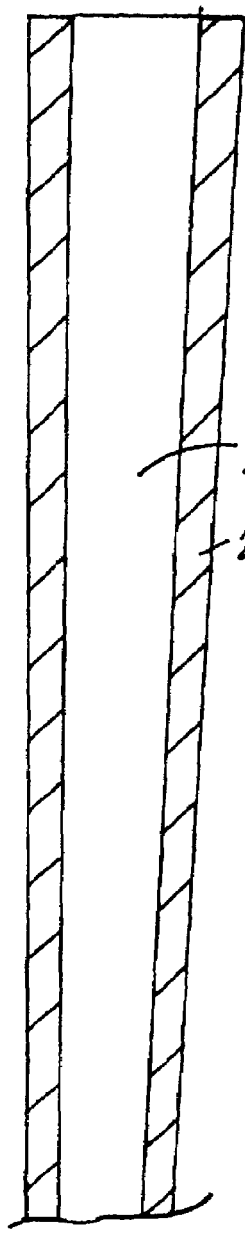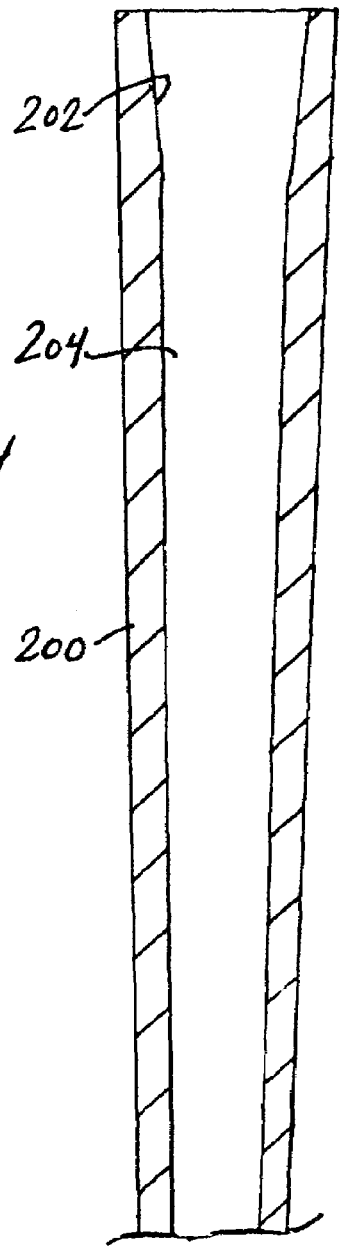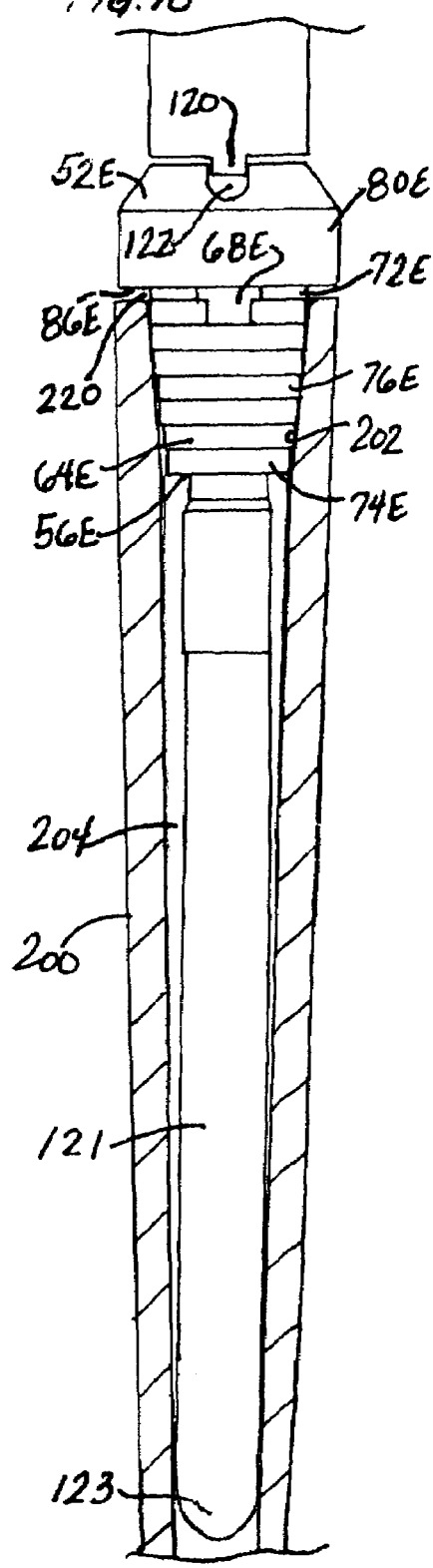

MODULAR IMPLANT SYSTEM AND METHOD WITH DIAPHYSEAL IMPLANT

CROSS-REFERENCE TO RELATED APPLICATIONS

The present invention claims priority to U.S. Provisional Patent Application Ser. No. 60/637,015, filed on Dec. 17, 2004 by Robert K. Heck and Stephen A. Hazebrouck and entitled "Modular Implant System and Method with Diaphyseal Implant," U.S. Provisional Patent Application Ser. No. 60/732,402, filed on Oct. 31, 2005 by Robert K. Heck and Stephen A. Hazebrouck and entitled "Modular Implant System and Method with Diaphyseal Implant and Adapter," and U.S. Provisional Patent Application Ser. No. 60/731,999, filed on Oct. 31, 2005 by Robert K. Heck and Stephen A. Hazebrouck, and entitled "Modular Diaphyseal and Collar Implant," all of which are incorporated by reference herein in its their entireties.

BACKGROUND OF THE INVENTION

The present invention relates generally to prosthetic joints and, more particularly, to modular orthopaedic lower extremity implant systems.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The distal femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

The hip joint consists of the bone interface of the proximal end of the femur and the acetabulum of the hipbone. The proximal femur is configured with a ball-shaped head, which is received within and articulates against the cup-shaped cavity defined by the acetabulum.

When the knee or hip joint is damaged whether as a result of an accident or illness, a prosthetic replacement of the damaged joint may be necessary to relieve pain and to restore normal use to the joint. Typically the entire joint is replaced by means of a surgical procedure, which involves removal of the surfaces of the corresponding damaged bones and replacement of these surfaces with prosthetic implants. This replacement of a native joint with a prosthetic joint is referred to as a primary total-knee arthroplasty and primary total-hip arthroplasty.

On occasion, the primary prosthesis fails. Failure can result from many causes, including wear, aseptic loosening, osteolysis, ligamentous instability, arthrofibrosis and patellofemoral complications. When the failure is debilitating, revision surgery may be necessary. In a revision, the primary prosthesis is removed and replaced with components of a revision prosthetic system.

Implant systems for both primary and revision applications are available from a variety of manufacturers, including DePuy Orthopaedics, Inc. of Warsaw, Ind. DePuy and others offer several different systems for both primary and revision applications. For example, DePuy Orthopaedics offers the P.F.C. SIGMA®) Knee System, the LCS® Total Knee System, and the S-ROM Modular Total Knee System. Each of these orthopaedic knee systems includes several components, some appropriate for use in primary knee arthroplasty and some appropriate for use in revision surgery.

DePuy Orthopaedics also offers other orthopaedic implant systems for other applications. One such system is the LPS System. The LPS System is provided for use in cases of neoplastic diseases (e.g., osteosarcomas, chondrosarcomas, giant cell tumors, bone tumors) requiring extensive resections and replacements of the proximal and/or distal femur, severe trauma, disease (e.g., avascular necrosis, osteoarthritis and inflammatory joint disease requiring extensive resection and replacement of the proximal and/or distal femur), and resection cases requiring extensive resection and replacement of the proximal, distal or total femur or proximal tibia (e.g., end-stage revision). Any of these conditions or a combination thereof can lead to significant amounts of bone loss. The LPS System provides components that can replace all or significant portions of a particular bone, such as the femur or tibia. The DePuy LPS System is described more fully in U.S. patent application Ser. No. 10/135,791, entitled "Modular Limb Preservation System", filed Apr. 30, 2002 by Hazebrouck et al., U.S. Pat. Publication No. US2003/0204267A1 (published Oct. 30, 2003), which is incorporated by reference herein in its entirety. Other companies also offer systems for similar indications.

The LPS system provides a comprehensive set of modular implants capable of addressing a wide range of orthopaedic conditions. Components of the LPS system can be combined in a variety of ways to account for variations in patient anatomy and differences in the amount of native bone remaining. As disclosed in U.S. Patent Publication No. US2003/0204267A1, the modular components can be combined to replace the proximal or distal femur, total femur, proximal tibia or the mid-shaft of a long bone. Similar systems can be used with other long bones, such as the bones of the upper arm.

Many of the combinations of components possible with the LPS system include stem components that are configured for implantation within the intramedullary canal of the remaining bone. Metaphyseal sleeves are available for use in the LPS system, as disclosed, for example, in U.S. patent application Ser. No. 10/817,051, entitled "Modular Implant System with Fully Porous Coated Sleeve", filed on Apr. 2, 2004 by Goodfried, Hazebrouck, Lester and Brown (U.S. Pat. Publication No. US2005/017883A1), which is incorporated by reference herein in its entirety. However, in some instances, the stem components must be used with implant components that have replaced the entire articulating portion of the bone and the metaphysis of the bone. In some indications, the remaining native bone comprises the diaphysis or shaft of the long bone, and a metaphyseal sleeve cannot be used.

An example of a long bone is illustrated in FIG. 1; in FIG. 1, the bone 10 is the femur. FIG. 2 illustrates the femur of FIG. 1 after the distal articulating end 12 and metaphysis 14 of the bone 10 have been removed due to neoplastic disease, trauma, disease or as part of an end-stage revision. The diaphysis of the bone is illustrated at 16 in FIGS. 1-2.

As shown in FIG. 2, the intramedullary canal 18 of the diaphysis 16 of the long bone 10 generally tapers, while the implant stem extensions 20 generally have parallel sides, such as those shown at 22, 24. As a result, the implant stem extension 20 frequently contacts the native bone tissue at the free end or tip 28 of the stem extension 20, while leaving gaps 30 along much of the length of the stem extension 20. Although these gaps 30 could be filled with bone cement, for optimal fixation it is desirable to use porous coated stem extensions. Such porous coated stem extensions tend to bind before becoming fully seated. Consequently, in cases where the stem extension is porous coated to encourage bone ingrowth, the bone ingrowth is frequently limited to the free end 28 of the stem. With bone ingrowth limited to the free end of the stem extension, there is stress shielding of the bone surrounding the remainder of the stem extension, and a long lever arm is created; both of these effects can lead to early loosening of the implant. Additionally, when significant ingrowth does occur and the stem extension must subsequently be removed, the procedure can be difficult.

SUMMARY OF THE INVENTION

The present invention addresses the need for an implant system that can be effectively used in the diaphyseal region of a long bone and for a surgical method for implanting a system in the diaphyseal region of a long bone.

In one aspect, the present invention addresses this need by providing a diaphyseal implant component comprising a first end, a second end with a bore, a longitudinal axis extending from the first end to the second end, and an outer surface including a first tapered portion at the first end and a second tapered portion at the second end. The bore is tapered and has a maximum inner dimension at the second end and a minimum inner dimension spaced between the first end and the second end of the implant component. The first tapered portion of the outer surface has a minimum outer dimension at the first end and a maximum outer dimension spaced from the first end. The second tapered portion of the outer surface has a minimum outer dimension at the second end and a maximum outer dimension spaced from the first end and second end. The second tapered portion has the same outer dimension along two perpendicular axes at the maximum outer dimension of the second tapered portion. The first tapered portion of the outer surface is smooth and the second tapered portion of the outer surface is porous.

In another aspect, the present invention addresses this need by providing a method of replacing a portion of a long bone having an articulating surface, an intramedullary canal and a diaphysis spaced from the articulating surface. The method comprises resecting the bone to remove a portion of the bone and leaving at least a portion of the diaphysis of the bone. A tapered bore is prepared in the diaphysis of the bone. An implant is provided comprising a diaphyseal portion and a stem portion. The stem portion is inserted into the intramedullary canal and the diaphyseal portion is inserted into the tapered bore in the diaphysis of the bone.

In another aspect, the present invention addresses this need by providing an orthopaedic implant kit for replacing a portion of a long bone, the long bone having an articulation portion, a diaphysis and an intramedullary canal. The kit includes a plurality of modular stems shaped to be received in the intramedullary canal of the long bone. Each stem has a free end and an opposite end to be connected to another implant component. The kit also includes a plurality of modular diaphyseal components capable of being connected to the modular stems. Each diaphyseal component includes a first end, a second end for connection to a selected modular stem, and a porous tapered outer surface. The porous tapered outer surface has a minimum outer diameter at the second end and a maximum outer diameter spaced from the second end. The second tapered portion has the same outer dimension along two perpendicular transverse axes at its maximum outer diameter.

BRIEF DESCRIPTION OF THE DRAWINGS

FIG. 1 is an anterior view of a left femur;

FIG. 2 is a cross-section of a portion of the diaphysis of the femur of FIG. 1, shown with a stem extension received in the intramedullary canal of the femur;

FIG. 3 is an elevation of a set of diaphyseal implant components of one embodiment of a set of orthopaedic implant components embodying the principles of the present invention;

FIG. 4 is an elevation of the set of diaphyseal implant components of FIG. 3, shown with the diaphyseal implant components turned ninety degrees about their longitudinal axes;

FIG. 5 is a longitudinal cross-section of one of the diaphyseal implant components of FIGS. 3-4 taken along line 5-5 of FIG. 3;

FIG. 6 is a longitudinal cross-section of another of the diaphyseal implant components of FIGS. 3-4, taken along line 6-6 of FIG. 3;

FIG. 7 is an end view of one of the diaphyseal implant components of FIGS. 3-4, taken along line 7-7 of FIG. 4;

FIG. 8 is an end view of one of the diaphyseal implant components of FIGS. 3-4, taken along line 8-8 of FIG. 3;

FIG. 9 is an exploded perspective view of a distal femoral implant assembly illustrating use of one of the diaphyseal implant components of FIGS. 3-4 in use with one style of stem extension;

FIG. 10 is an exploded perspective view similar to FIG. 9, but illustrating use of one of the diaphyseal implant components of FIGS. 3-4 in use with an adapter and a different style of stem extension;

FIG. 11 is a side view of a distal femoral implant assembly including one of the diaphyseal implant components of FIGS. 3-4 in use with a different style of stem extension;

FIG. 12 is a posterior view of the distal femoral implant assembly of FIG. 11;

FIG. 15 is a side view of an intercalary implant assembly including two of the diaphyseal implant components of FIGS. 3-4;

FIG. 15A is a side view of an intercalary implant assembly including one of the diaphyseal implant components of FIGS. 3-4;

FIG. 16 is a diagrammatic cross-section of a portion of the remaining portion of the diaphysis after a portion of the femur or long bone has been resected;

FIG. 17 illustrates the remaining resected diaphysis of FIG. 16 after a tapered bore has been prepared at the resection site of the bone; and FIG. 18 illustrates the remaining resected diaphysis of FIG. 17 with an implant assembly including a diaphyseal implant component fully seated in the bone.

DETAILED DESCRIPTION

Figure 13:
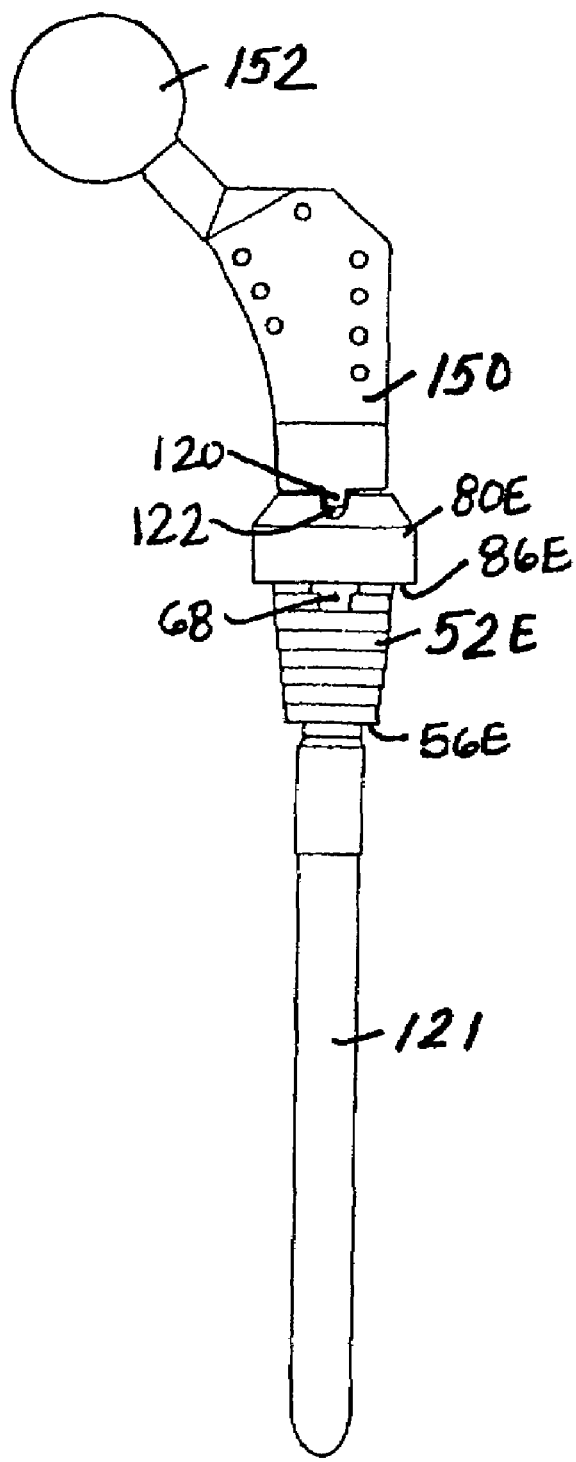
FIG. 13 is a side view of a proximal femoral implant assembly including one of the diaphyseal implant components of FIGS. 3-4.

A modular orthopaedic knee implant system incorporating the principles of the present invention is illustrated in the accompanying drawings. The illustrated modular orthopaedic knee implant system includes components of several existing orthopaedic knee implant systems, along with new components that provide the orthopaedic surgeon with greater flexibility in selecting the appropriate components to suit the needs of an individual patient. These patient needs can include factors such as individual anatomy and the condition of the native bone tissue.

FIGS. 3-4 illustrate a set 50 of diaphyseal implant components that can be used in the system or kit of the present invention. The illustrated set 50 of diaphyseal implant components includes five sizes of diaphyseal components, labeled 52A, 52B, 52C, 52D, 52E. The illustrated diaphyseal components 52A, 52B, 52C, 52D, 52E include several common features. In the following description and in the drawings, like parts are identified with the same reference number, followed by a letter designation to identify the particular size of component.

Each of the illustrated diaphyseal components 52A, 52B, 52C, 52D, 52E has an annular first end 54A, 54B, 54C, 54D, 54E an annular second end 56A, 56B, 56C, 56D, 56E and a longitudinal axis 58A, 58B, 58C, 58D, 58E extending from the first annular end 54A, 54B, 54C, 54D, 54E to the second annular end 56A, 56B, 56C, 56D, 56E. Each of the illustrated diaphyseal components 52A, 52B, 52C, 52D, 52E also has an outer surface 60A, 60B, 60C, 60D, 60E.

The outer surface 60A, 60B, 60C, 60D, 60E of each of the illustrated diaphyseal components 52A, 52B, 52C, 52D, 52E, 52F has a first tapered portion 62A, 62B, 62C, 62D, 62E at the first annular end 54A, 54B, 54C, 54D, 54E and a second tapered portion 64A, 64B, 64C, 64D, 64E at the second annular end 56A, 56B, 56C, 56D, 56E.

The first tapered portion 62A, 62B, 62C, 62D, 62E of each diaphyseal component 52A, 52B, 52C, 52D, 52E has a minimum outer diameter at the first annular end 54A, 54B, 54C, 54D, 54E and a maximum outer diameter spaced from the first annular end 54A, 54B, 54C, 54D, 54E. The first tapered portion 62A, 62B, 62C, 62D, 62E is smooth, and defines a male Morse taper post, similar to the Morse taper posts described and shown in Modular Limb Preservation System, U.S. Pat. Publication No. US2003/0204267A1. The first tapered portion is sized and shaped to be received within and to lock through a friction fit with a Morse taper bore provided in one of the other implant components of the system, such as a modular articulation component like the distal femoral component shown in FIG. 9-12, the proximal femoral component shown in FIG. 13 or the tibial component shown in FIG. 14. The first tapered portion can also be received within and to frictionally lock with a segmental component such as those shown in FIGS. 9-13 including an intercalary component as shown in FIG. 15. Thus, the diaphyseal components 52A, 52B, 52C, 52D, 52E are each capable of interlocking with other components of the system. Accordingly, the first tapered portion of each of the diaphyseal components is of like shape and size so that any of the sizes of the diaphyseal components can be used with any of the other modular components of the system having the corresponding female taper.

The second tapered portion 64A, 64B, 64C, 64D, 64E of each diaphyseal implant component 52A, 52B, 52C, 52D, 52E in the set 50 is of a different size to accommodate the needs of the individual patient's anatomy. The illustrated set includes sizes ranging from extra-small 52A to extra-large 52E.

The second tapered portion 64A, 64B, 64C, 64D, 64E of each diaphyseal implant component 52A, 52B, 52C, 52D, 52E in the set 50 has a minimum outer diameter at the second end 56A, 56B, 56C, 56D, 56E and a maximum outer diameter spaced from the first annular end 54A, 54B, 54C, 54D, 54E and the second annular end 56A, 56B, 56C, 56D, 56E. The maximum outer diameter is indicated at 66A, 66B, 66C, 66D, 66E in FIGS. 3-4.

The second tapered portion 64A, 64B, 64C, 64D, 64E has a plurality of flats 68A, 68B, 68C, 68D, 68E at the maximum outer diameter 66A, 66B, 66C, 66D, 66E. The flats are provided to help to limit rotation of the diaphyseal components 52A, 52B, 52C, 52D, 52E with respect to the bone after implantation, as described in more detail below. It should be understood that the diaphyseal implant components could be provided without such flats if desired.

FIG. 8 illustrates an end view of one of the diaphyseal implant components 52B of the set 50, taken from the second end 56B of the component. As there shown, the second tapered portion 64B has four equally spaced flats 68B connected by curved arcs 70B. The maximum outer dimensions of the second tapered portion 64B are shown at $d_1$ and $d_2$ in FIG. 8; in the illustrated embodiments, $d_1=d_2$. Thus, the second tapered portion 64B has the same outer dimension $d_1$, $d_2$ along two perpendicular transverse axes at the maximum outer dimension 66B of the second tapered portion 64B.

In the smallest size of diaphyseal implant component 52A, the outer surface of most of the second tapered portion 64A has a frustoconical shape, shown at 71A in FIGS. 3-4. Frustoconical is intended to mean shaped like the frustum of a cone, that is, it has the shape of the basal part of a solid cone formed by cutting off the top by a plane parallel to the base. In each of the other sizes of diaphyseal implant components 52B, 52C, 52D, 52E in the set 50, the outer surface of the second tapered portion 64B, 64C, 64D, 64E comprises a plurality of annular steps: there is a first annular step 72B, 72C, 72D, 72E between the first end 54B, 54C, 54D, 54E and second end 56B, 56C, 56D, 56E of the diaphyseal implant components, a last annular step 74B, 74C, 74D, 74E at the second end 56B, 56C, 56D, 56E of the diaphyseal implant component and a plurality of intermediate annular steps 76B, 76C, 76D, 76E between the first step 72B, 72C, 72D, 72E and last step 74B, 74C, 74D, 74E. The smallest size of diaphyseal implant component 52A also has a first annular step 72A at its maximum outer diameter 66A adjacent to the frustoconical portion of the second tapered portion 64A.

Each annular step 72A, 72B, 72C, 72D, 72E, 74B, 74C, 74D, 74E, 76B, 76C, 76D, 76E has a substantially cylindrically shaped outer surface and a longitudinal height; the largest diameter steps deviate from a cylindrical shape in the illustrated embodiments because of the presence of the four flats 68. In each illustrated size of diaphyseal implant component, the first annular step 72A, 72B, 72C, 72D, 72E has the greatest maximum outer diameter, and the maximum outer diameter of each step progressively decreases to the last annular step 74B, 74C, 74D, 74E which has the smallest maximum outer diameter. In the illustrated set of diaphyseal implant components 52A, 52B, 52C, 52D, 52E examples of sizes and numbers of steps are provided in the following table:

| Extra Extra Small Diaphyseal Implant Component 52A | | | |
| --- | --- | --- | --- |
| | Height | Outer Diameter | Taper Angle |
| First step 72A | 2 mm | 12.95 mm | — |
| Frustoconical Portion 71A | 15.04 mm | 12.65 mm maximum to 10.67 mm minimum | 3° |

| Extra Small Diaphyseal Implant Component 52B | | | |
| --- | --- | --- | --- |
| | Step Height | Step Outer Diameter | Overall Taper Angle |
| First step 72B | 2 mm | 15.23 mm | 4°52' |
| Second step | 4 mm | 14.37 mm | |
| Third step | 4 mm | 13.51 mm | |
| Fourth step | 4 mm | 12.65 mm | |
| Last step 74B | 4 mm | 11.79 mm | |

-continued

Small Diaphyseal Implant Component 52C

|  | Step Height | Step Outer Diameter | Overall Taper Angle |
|---|---|---|---|
| First step 72C | 2 mm | 19.09 mm | 4°33' |
| Second step | 4 mm | 18.37 mm |  |
| Third step | 4 mm | 17.65 mm |  |
| Fourth step | 4 mm | 16.93 mm |  |
| Fifth step | 4 mm | 16.21 mm |  |
| Last step 74C | 4 mm | 15.49 mm |  |

Medium Diaphyseal Implant Component 52D

|  | Step Height | Step Outer Diameter | Overall Taper Angle |
|---|---|---|---|
| First step 72D | 2 mm | 22.53 mm | 6°35' |
| Second step | 4 mm | 21.51 mm |  |
| Third step | 4 mm | 20.49 mm |  |
| Fourth step | 4 mm | 19.47 mm |  |
| Fifth step | 4 mm | 18.45 mm |  |
| Sixth step | 4 mm | 17.43 mm |  |
| Last step 74D | 4 mm | 16.41 mm |  |

Large Diaphyseal Implant Component 52E

|  | Step Height | Step Outer Diameter | Overall Taper Angle |
|---|---|---|---|
| First step 72E | 2 mm | 26.51 mm | 6°39' |
| Second step | 4 mm | 25.49 mm |  |
| Third step | 4 mm | 24.47 mm |  |
| Fourth step | 4 mm | 23.45 mm |  |
| Fifth step | 4 mm | 22.44 mm |  |
| Sixth step | 4 mm | 21.42 mm |  |
| Seventh step | 4 mm | 20.40 mm |  |
| Last step 74E | 4 mm | 19.38 mm |  |

In the above table, the Overall Taper Angle refers to the angle defined by a line tangent to the steps 72, 74, 76 and a line parallel to the longitudinal axis 58 in each size.

It should be understood that the sizes, numbers of steps and overall taper angles identified in the above tables are provided as examples only. The present invention is not limited to a stepped configuration or to any particular size, number of steps or overall angle of taper unless expressly called for in the claims. Moreover, although five sizes are illustrated in the set 50, fewer or more sizes could be provided; the invention is not limited to any number of sizes of implant components unless expressly called for in the claims.

In each of the illustrated diaphyseal implant components 52A, 52B, 52C, 52D, 52E, most of the entire second tapered portion, including the entire frustoconical portion of the small implant component 52A to all of the steps of the other sizes of implant components 52B, 52C, 52D, 52E, 52F is porous. The last or smallest diameter step 74 is not porous in these embodiments, and the last 2 mm of the smallest diaphyseal implant 52A is not porous. As used herein, "porous" refers to a surface that is conducive to bone ingrowth for non-cemented fixation, and "smooth" refers to a surface that is not conducive to such bone ingrowth. Suitable porous surfaces can be made by many different methods: casting, embossing, etching, milling, machining, and coating such as by plasma-spraying or by bonding, for example. Bonded materials can comprise sintered metal beads, sintered metal mesh or screen, or sintered metal fibers, for example. Known, commercially available materials and techniques can be used to create the porous tapered surfaces of the diaphyseal components: for example, POROCOAT® coating, available from DePuy Orthopaedics, Inc. of Warsaw, Ind., could be used, as well as other commercially available coatings. In addition, the porous surfaces may include other materials conducive to bone ingrowth, such as hydroxy apatite coatings, for example. It should be understood that the above-identified examples of materials, methods and commercial products are provided as examples only; the present invention is not limited to any particular material, method or commercial product for the porous surfaces unless expressly called for in the claims. In addition, it should be understood that as additional materials and methods become available to create surfaces that promote bony ingrowth, it is believed that such other materials and methods may also be useful with the present invention.

Each of the four flats 68A, 68B, 68C, 68D, and 68E in each illustrated size is 6 mm high. The flats are disposed at 90° intervals around the first step and second step in the diaphyseal implant components 52B, 52C, 52D, 52E, 52F that have stepped second tapered surfaces, and are also disposed at 90° intervals around the tapered frustoconical surface of the smallest implant component. It should be understood that the flats may have different dimensions and different positions.

As shown in FIGS. 3-4, each size of diaphyseal implant components 52A, 52B, 52C, 52D, 52E in the set 50 has an annular collar 80A, 80B, 80C, 80D, 80E disposed between the first tapered portion 62A, 62B, 62C, 62D, 62E and the second tapered portion 64A, 64B, 64C, 64D, 64E of the outer surface 60A, 60B, 60C, 60D, 60E of the implant component. The annular collars 80A, 80B, 80C, 80D, 80E have outer diameters greater than the maximum outer diameter of the first tapered portion 62A, 62B, 62C, 62D, 62E and greater than the maximum outer diameter of the second tapered portion 64A, 64B, 64C, 64D, 64E. In each of the illustrated sizes, at least a portion of the outer surface of each collar is cylindrical in shape: in the extra extra small component 52A, all or substantially all of the outer surface of the collar 80A is cylindrical in shape; in the other sizes 52B, 52C, 52D, 52E the collars 80B, 80C, 8D, 80E include a cylindrical portion 82B, 82C, 82D, 82E adjacent to the second tapered portion 64B, 64C, 64D, 64E and a frustoconical portion 84B, 84C, 84D, 84E adjacent to the first tapered portion 62B, 62C, 62D, 62E. A portion or all of each collar 80A, 80B, 80C, 80D, 80E may be porous; for example, an annular porous strip having a height (longitudinal dimension) of 10 mm may be provided on the cylindrical portions 82A, 82B, 82C, 82D, 82E for soft tissue attachment and ingrowth. Variations in the type and characteristics of the porous coating may be made to encourage soft tissue ingrowth, as opposed to bone ingrowth. Moreover, features may be included on the collar to allow for attachment of soft tissue or the periosteum; for example, suture holes may be provided on the collar.

Each collar 80A, 80B, 80C, 80D, 80E includes a transverse annular surface 86A, 86B, 86C, 86D, 86E that is perpendicular to the longitudinal axis 58A, 58B, 58C, 58D, 58E of the diaphyseal implant component. The transverse annular surface 86A, 86B, 86C, 86D, 86E is sized and provides a surface area sufficient to bear against the resected end of the bone if the diaphyseal implant component subsides. For example, the transverse annular surface 86A, 86B, 86C, 86D, 86E may have an outer diameter in the range of about 1 inch to 1½ inch (25.4 mm to 38.1 mm) and an inner diameter at the first step 72A, 72B, 72C, 72D, 72E in the range of about ½ inch to 1 inch (12.7 mm to 25.4 mm), thus providing surface areas in the range of about 0.59 square inches to about 0.98 square inches (about 380 mm$^2$ to about 633 mm$^2$). With a porous coating, the diameters should increase by about sixty-thousandths of an inch (1.5 mm) It should be understood that these dimensions are provided as examples only; the present invention is not limited to any particular dimension unless expressly called for in the claims. The transverse annular surface 86A, 86B, 86C, 86D, 86E may be porous or smooth; if porous, the transverse annular surface may provide a surface conducive to tissue ingrowth.

Representative cross-sections of the diaphyseal implant components 52A, 52B, 52C, 52D, 52E are illustrated in FIGS. 5-6. It should be understood that cross-sections of other sizes of diaphyseal implant components may be similar to those shown in FIGS. 5-6.

Each of the diaphyseal implant components 52A, 52B, 52C, 52D, 52E has a throughbore extending longitudinally through the entire length of the component, from the first annular end 54A, 54B, 54C, 54D, 54E to the second annular end 56A, 56B, 56C, 56D, 56E. Examples of throughbores are shown at 90A, 90B and 90C in FIGS. 5-8. In the extra-extra small and extra-small sizes 52A, 52B, the throughbore has a threaded portion (shown at 92A in FIG. 5) to receive the threaded end of a stem extension. In the other larger sizes 52C, 52D, 52E, the portion of the throughbore near the second annular end 56C, 56D, 56E comprises a Morse taper bore sized and shaped to receive a Morse taper post at the end of a stem extension or at the end of an adapter. An example of such a Morse taper bore is shown at 94C in FIG. 6. It should be understood that the illustrated longitudinal throughbores are provided as examples only; other designs could be employed, depending on the desired wall thickness for the implant and the type of connection to be employed to the other implant components.

FIGS. 9-10 illustrate the large size diaphyseal implant component 52E in exploded views with other modular implant components that may be included in a kit or system and assembled with the diaphyseal implant component 52 for implantation. In FIGS. 9-10, the assembly is intended for use in replacing a portion of the distal femur. The assemblies of both FIGS. 9 and 10 include a distal femoral implant 100, a segmental implant component 102, a diaphyseal implant component 52 (the large size 52E is illustrated).

Each assembly also includes a stem extension. In FIG. 9, the stem extension 104 has a coronal-slotted free end or tip 106, a body 107 and a connection end 108. The connection end 108 comprises a Morse taper post in the embodiment of FIG. 9. The Morse taper post at the connection end 108 is received within and frictionally locks with the Morse taper bore of the diaphyseal implant component 52E. In FIG. 10, the stem extension 110 has a free end or tip 112, a body 113 and a connection end 114 that comprises a male threaded member. The embodiment of FIG. 10 also includes an adapter 116 with a threaded opening (not shown) to receive the male threaded connection end 114 of the stem extension and a Morse taper post 118 to be received in the Morse taper bore of the diaphyseal implant component 52E. All of the large size diaphyseal implant components 52C, 52D, 52E can be assembled with stem extensions in the manners illustrated in FIGS. 9-10. Due to constraints on the thicknesses of the walls of the second tapered portions 64A, 64B of the smaller sized diaphyseal implant components 52A, 52B, accommodation is only made for connection to a stem extension with a threaded male end of the type shown in FIG. 10.

The bodies 107, 113 of the stem extensions 104, 110 may vary. For example, a substantial part of the length of the body, such as body 107 of FIG. 9, can be porous. Alternatively, the body can be sized and shaped for cemented application, like the body 113 of the stem extension 110 of FIG. 10. Alternatively, the body of the stem extension can be splined.

FIGS. 11-12 illustrate a stem extension 115 with a coronal slotted free end 117, a splined body 119, and a connection end (not shown) comprising a Morse taper post. In the embodiment of FIGS. 11-12, the splined body 119 of the stem extension 115 comprises a plurality of cutting flutes. The stem extension 115 of FIGS. 11-12 is not porous. Although in FIGS. 11-12 the free end 117 of the stem extension 115 is illustrated as being substantially flat, it may be desirable for the free end 117 to be bullet-shaped.

Features of the adapter 116 are disclosed in more detail in U.S. patent application Ser. No. 10/817,051 entitled "Modular Implant System with Fully Porous Coated Sleeve", filed on Apr. 2, 2004 by Goodfried, Hazebrouck, Lester and Brown (U.S. Pat. Publication No. US2005/0107883A1), the complete disclosure of which is incorporated by reference herein.

As disclosed in U.S. Pat. Publication No. US2003/0204267A1, the distal femoral implant component 100 and segmental component 102 both include tabs 120. Each of the diaphyseal implant components 52A, 52b, 52C, 52D, 52E include corresponding notches 122 to receive the tabs 120 to prevent the diaphyseal implant components from rotating. These notches can also be used to separate the components if necessary; a tool such as that disclosed in U.S. Pat. No. 6,786,931 may be used.

It should be understood that a typical implant kit or system would include several sizes of distal femoral implant components 100, segmental components 102 and stem extensions 104, 110. It should also be understood that depending on the size and shape of the distal femoral component, it may not be necessary to use a segmental component 102; the diaphyseal implant component 52A, 52B, 52C, 52D, 52E could be connected directly to the femoral implant component 100.

Figure 14:
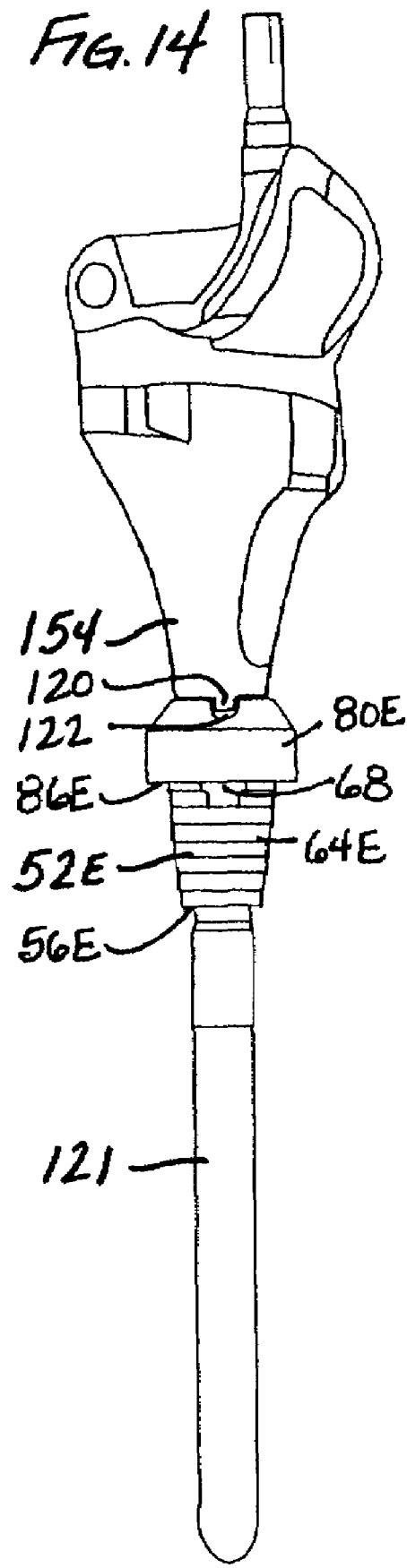
FIG. 14 is a perspective view of a proximal tibial implant assembly including one of the diaphyseal implant components of FIGS. 3-4.

Use of the diaphyseal implant components 52A, 52B, 52C, 52D, 52E of the present invention is not limited to segmental components and femoral components. As illustrated in FIGS. 13-15A, the diaphyseal implant components of the present invention can be used with other implant components having an articulation portion. For example, as shown in FIG. 13, the articulation portion of the implant component could comprise a proximal femoral component 150 (including a femoral head 152). As shown in FIG. 14 the articulation portion of the implant component could comprise a proximal tibia component 154 or other component, such as a proximal humeral component (not shown).

As shown in FIGS. 15-15A, the implant component could be an intercalary implant instead of an articulation component. FIG. 15 illustrates two large size diaphyseal implant components 52E in use with a two-piece intercalary implant 156 of the type disclosed in U.S. application Ser. No. 10/403,612 entitled "Intercalary Prosthesis, Kit and Method," filed Mar. 31, 2003 by Hazebrouck (U.S. Pat. Publication No. US2004/0193268A1), incorporated by reference herein in its entirety, or those disclosed in U.S. application Ser. No. 10/403,357 entitled "Intercalary Implant," filed on Mar. 31, 2003 by Natalie Heck and Michael C. Jones (U.S. Pat. Publication No. US2004/0193267A1) (also incorporated by reference herein in its entirety). Such implants may be used with intercalary trials such as those disclosed in U.S. patent application Ser. No. 10/952,581, entitled "Orthopaedic Spacer," filed on Sep. 24, 2004 by Hazebrouck (U.S. Pat. Publication No. US2005/0107794A1), the complete disclosure of which is incorporated by reference herein. FIG. 15A illustrates a single diaphyseal implant components in use with the two-piece intercalary component 156 and a standard stem extension 157 for the LPS implant system.

In FIGS. 13-15A the stem extension is shown diagrammatically and indicated generally by reference number 121, with the free end indicated by reference number 123. Other than the bullet shape of the free end 123, no other features are shown for the body 125 of the stem extension. It should be understood that the body 125 of the stem extension 121 in any of FIGS. 13-15A could have any of the above described features, such as splined cutting flutes, a porous coating, a coronally slotted free end, or could be designed for cemented application.

All of the components of the illustrated implant systems can be made of standard materials for such implants, such as titanium and cobalt-chrome alloys.

It should be understood that although the principles of the present invention are described and illustrated with reference to implant components available from DePuy Orthopaedics, Inc., the invention is not limited to these components or their features. The principles of the present invention can be applied to other implant components, including those of other manufacturers and those subsequently developed.

In use, depending on the condition of the native bone tissue, the orthopaedic surgeon will determine the amount of bone to be resected from the femur (or other long bone). Commercially available instrumentation can be used to resect the bone in the appropriate manner. The diaphysis of a resected bone is illustrated in FIGS. 16-18 at 200. If it is desirable to use a diaphyseal implant component 52A, 52B, 52C, 52D, 52E to secure the implant in place, the surgeon can then select an appropriate size of diaphyseal implant component 52A, 52B, 52C, 52D or 52E for the individual patient. The diaphysis 200 of the bone can then be prepared to receive the selected diaphyseal implant component 52A, 52B, 52C, 52D or 52E. The surgeon can use a conical reamer (not shown) of a size and shape matching the size and shape of the selected diaphyseal component to mill or machine the diaphysis 200 of the bone to create a tapered bore that closely matches the size and shape of the second tapered surface 64A, 64B, 64C, 64D, 64E of the selected diaphyseal implant component. A tapered bore is illustrated in FIGS. 17-18 at 202. Since the tapered bore is created to match the size and shape of the selected diaphyseal implant component, the implants and techniques of the present invention are adaptable to different patient anatomies.

The stem extension and part of the diaphyseal implant component of the assembled implant, can then be inserted into the bone as illustrated in FIG. 18 and positioned with the tip or free end of the stem extension engaging the bone surface of the intramedullary canal 204 and with the second tapered portion 64A, 64B, 64C, 64D or 64E bearing against the tapered diaphyseal bone defining the tapered bore 202. The stem extension in FIG. 18 is identified with reference number 121 and its free end is identified with reference number 123; as discussed above with respect to FIGS. 13-15A, the stem extension 121 is illustrated diagrammatically, and can include any of the features of the stem extensions 104, 110, 115 described above. Because of the shapes and textures of the implant components 121, 52A, 52B, 52C, 52D or 52E, there should be no binding before the diaphyseal component 52A, 52B, 52C, 52D or 52E is fully seated. Accordingly, implantation should be relatively easy.

Generally, when implanted, the first step 72A, 72B, 72C, 72D, 72E of each of the diaphyseal implant components 52A, 52B, 52C, 52D, 52E will be exposed outside of the bone as shown in FIG. 18. Subsequently, some subsidence of the implant can occur over time without damage to the bone. The flats 68E prevent the diaphyseal component 52E from rotating or turning in the tapered bore 202 that the surgeon created for it.

As shown in FIG. 18, when fully seated, the implant assembly contacts the bone at both the tip 123 of the stem extension 121 and at the second tapered outer surface 64E of the diaphyseal component 52E. Bone ingrowth can occur around the entire second tapered portion 64E of the diaphyseal implant component 52E. Depending on the intramedullary canal anatomy and characteristics of the stem extension, bone ingrowth can also occur along all or part of the body of the stem; for example, bone ingrowth could occur at the free end of the stem extension and/or at any area between the diaphyseal component and the free end of the stem. For example, if a cemented stem extension is used, such as the stem extension 110 of FIG. 10, there should be no bone ingrowth along the body of the stem. Similarly, no substantial bone ingrowth should occur along the stem with the splined stem extension 115 of FIGS. 11-12. If all or part of the stem extension 104 of FIG. 9 is porous, bone ingrowth can be expected at the porous area.

With the stepped designs of the larger diaphyseal implant components, such as diaphyseal implant components 52B, 52C, 52D, 52E, shear forces are essentially converted to compressive loads, and the compressive loads are spread among the steps 74, 76 contacting the diaphyseal bone defining the tapered bore 202. Accordingly, the implant is immediately stable and capable of bearing weight. In addition, with the bone bearing the axial load at the diaphyseal bone defining the tapered bore 202, there is no disadvantageous stress shielding of the bone. Moreover, with the implant assembly contacting the bone at both the tip 106 of the stem extension and at the contacting surfaces of the tapered bore 202 and second tapered surface 64, any moment arm is significantly reduced if not eliminated. With bone ingrowth occurring at both spaced locations over time, long term implant stability should be improved. Accordingly, the implant assembly of the present invention should be less likely to loosen over time.

As can be seen in FIG. 18, a small gap 220 may be between the exposed resected bone surface and the transverse annular surface 86E of the collar 80E portion of the component 52E when implanted. If the implant does subside, this gap can decrease to the point that the transverse annular surface 86E bears directly against the exposed resected bone surface. If the transverse annular surface is porous, tissue ingrowth can occur in the gap 220 over time to seal the intramedullary canal 204 against debris.

With any of the illustrated diaphyseal implant components, the periosteum of the bone should grow into the porous outer surface of the collar portion 80 of the diaphyseal implant component 52. Essentially the ingrowth of tissue along the cylindrical outer surface of the collar (or along the exposed portion of the transverse annular surface of the collar) should effectively seal off the intramedullary canal 204, to thereby protect the patient from injury or disease resulting from debris entering into the intramedullary canal.

Moreover, with the modular implant system of the present invention, it should be possible to reduce inventory of the necessary parts in an implant system or kit.

It should also be understood that a typical surgical kit would also include trial implant components (not shown) like those shown in FIGS. 3-4 and 9-15. The surgeon would typically assemble a trial implant and temporarily secure the trial implant assembly in place on the prepared diaphyseal bone to ensure that the assembled implant will be the optimum for the individual patient's needs. The trial components can have features like those described above for the final implant components.

In case it is necessary to ultimately remove the implant assembly from the patient, such removal should not require the removal of excessive bone stock, since it should only be necessary to remove the portion of the diaphysis defining the tapered bore 202.

Various modifications and additions can be made to the above-described embodiments without departing from spirit of the invention. All such modifications and additions are intended to fall within the scope of the claims unless the claims expressly call for a specific construction.

We claim:

1. A diaphyseal implant component comprising:
   a first end;
   a second end with a bore and an annular surface;
   a longitudinal axis extending from the first end to the second end, the annular surface of the second end being perpendicular to the longitudinal axis; and an outer surface including a first tapered portion extending from the first end and a second tapered portion extending from the annular surface of the second end; wherein the bore is tapered and has a maximum inner dimension at the second end and a minimum inner dimension spaced between the first end and the second end of the implant component;

the first tapered portion of the outer surface has a frusto-conical shape with a minimum outer dimension at the first end and a maximum outer dimension spaced from the first end;

the second tapered portion of the outer surface has a minimum outer dimension at the second end and a maximum outer dimension spaced from the first end and second end;

the second tapered portion has the same outer dimension along two perpendicular transverse axes at the maximum outer dimension of the second tapered portion; and the first tapered portion of the outer surface is smooth and the second tapered portion of the outer surface is porous; and the second tapered portion of the outer surface comprises a plurality of steps, each step having a maximum outer dimension and a height, the step nearest the second end having the smallest outer dimension and the step nearest the first end having the largest outer dimension.

2. The diaphyseal implant component of claim 1 further comprising an annular collar disposed between the first tapered portion of the outer surface and the second tapered portion of the outer surface, the annular collar having an outer diameter greater than the maximum outer dimension of the first tapered portion of the outer surface and greater than the maximum outer dimension of the second tapered portion of the outer surface, and wherein a plurality of the steps of the second tapered portion are exposed.

3. The diaphyseal implant component of claim 2 wherein at least a portion of the outer surface of the collar is porous.

4. The diaphyseal implant component of claim 2 wherein the collar has an outer surface including a portion having a cylindrical shape.

5. The diaphyseal implant component of claim 4 wherein the outer surface of the collar includes a portion having a frustoconical shape.

6. The diaphyseal implant component of claim 5 wherein at least a portion of the cylindrically-shaped outer surface of the collar is porous.

7. The diaphyseal implant component of claim 1 wherein the plurality of steps include a first step between the first end of the implant component and the second end of the implant component, a last step at the second end of the implant component and an intermediate step between the first step and last step, each step having a maximum outer dimension and a longitudinal height, the maximum outer dimension of the second tapered portion of the implant component being at the first step and the minimum outer dimension of the second tapered portion of the implant component being at the last step.

8. The diaphyseal implant component of claim 7 wherein the height of the first step is less than the height of the last step and less than the height of the intermediate step.

9. The diaphyseal implant component of claim 8 wherein the height of the first step is about 2 mm.

10. The diaphyseal implant component of claim 7 wherein the surface of each step is fully porous coated.

11. The diaphyseal implant component of claim 1 wherein the implant component is part of a kit including a plurality of diaphyseal implant components of different size.

12. The diaphyseal implant component of claim 1 wherein the diaphyseal implant component is part of a kit including a stem for attachment to the second end of the diaphyseal implant component and another implant component having a different shape than the stem and the diaphyseal implant component for attachment to the first end of the diaphyseal implant component.

13. The diaphyseal implant component of claim 7 further comprising an annular collar adjacent to the first step, the annular collar extending from the first step to the maximum outer dimension of the first tapered portion, wherein the first step has the same outer diameter along two perpendicular transverse axes at the maximum outer dimension of the second tapered portion and wherein the first step, last step and intermediate step are exposed.

14. A diaphyseal implant component comprising:
a first end including a tapered post;
a second end with a bore and an annular end surface; and
a longitudinal axis extending from the first end to the second end;
wherein
the bore is tapered and has a maximum inner dimension at the second end and a minimum inner dimension spaced between the first end and the second end of the implant component;
the tapered post has a minimum outer dimension at the first end and a maximum outer dimension spaced from the first end;
an annular end step having a cylindrical outer surface extending from the annular end surface of the second end toward the first end, the cylindrical outer surface having a maximum outer dimension and a height, the cylindrical outer surface having the same outer dimension along two perpendicular transverse axes at the maximum outer dimension;
an annular adjacent step extending from the end step, the adjacent step having a cylindrical outer surface having a maximum outer dimension and a height, the cylindrical outer surface having the same outer dimension along two perpendicular transverse axes at the maximum outer dimension, the maximum outer dimension of the adjacent step being greater than the maximum outer dimension of the end step.

15. The diaphyseal implant component of claim 14 wherein the outer surface of the end step is non-porous and the outer surface of the adjacent step is porous.

16. The diaphyseal implant component of claim 14 wherein the height of the end step is less than 5 mm.

17. The diaphyseal implant component of claim 14 further comprising a first step between the adjacent step and the first end of the component, the first step including an outer surface having a plurality of flats connected by curved surfaces, the first step having a maximum outer dimension and a height, the outer surface of the first step having the same outer dimension along two perpendicular transverse axes at the maximum outer dimension, the maximum outer dimension of the first step being greater than the maximum outer dimension of the end step and the adjacent step.

18. The diaphyseal implant component of claim 17 wherein the end step has a non-porous outer surface and the adjacent step and first step have porous outer surfaces.

19. The diaphyseal implant component of claim 17 further comprising an annular collar disposed between the first step and the maximum outer dimension of the tapered post, the annular collar having an outer diameter greater than the maximum outer dimension of the tapered post and greater than the maximum outer dimension of the first step.

20. The diaphyseal implant component of claim 19 wherein the first step is adjacent to the annular collar and exposed.

21. The diaphyseal implant component of claim 20 wherein the collar has a transverse annular surface adjacent to the first step and perpendicular to the longitudinal axis of the diaphyseal implant component.

* * * * *